(12) United States Patent
Saito et al.

(10) Patent No.: US 6,475,201 B2
(45) Date of Patent: Nov. 5, 2002

(54) DISPOSABLE UNDERWEAR

(75) Inventors: Akiko Saito, Kagawa (JP); Michiyo Fujikawa, Kagawa (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 10/050,268

(22) Filed: Jan. 16, 2002

(65) Prior Publication Data

US 2002/0099345 A1 Jul. 25, 2002

(30) Foreign Application Priority Data

Jan. 19, 2001 (JP) ........................................ 2001-011893

(51) Int. Cl.[7] ................................................ A61F 13/15
(52) U.S. Cl. ...................................... 604/385.01; 2/400
(58) Field of Search ................ 2/400–406; 604/317–402

(56) References Cited

U.S. PATENT DOCUMENTS 2,427,906 A * 9/1947 Golightly et al. ............... 2/400
5,733,635 A * 3/1998 Terakawa et al. ............... 2/400

* cited by examiner

Primary Examiner—Jeanette Chapman
(74) Attorney, Agent, or Firm—Baker & Daniels

(57) ABSTRACT

A disposable underwear is formed by laying a front body and a back body one on top of the other, providing a bonded portion on at least one of the left and right side edges, and providing leg openings and a waist opening. The disposable underwear includes a tightening member in the vicinity of the waist opening. The front and back bodies further comprise a non-bonded portion formed at the portion between the tightening member and the bonded portion.

10 Claims, 5 Drawing Sheets

DISPOSABLE UNDERWEAR

CROSS REFERENCE TO RELATED APPLICATION

This application claims the priority of Application No. 2001-011893, filed Jan. 19, 2001 in Japan, the subject matter of which is incorporated herein by reference.

TECHNICAL FIELD OF THE INVENTION

The present invention relates to an underwear to be worn by a patient before surgery in the hospital, and more specifically, to a disposable underwear for wearing on the lower body.

BACKGROUND OF THE INVENTION

Conventionally, there is underwear just like a loincloth called T-shaped band as disposable underwear to be worn by a patient who is to be undergone medical procedure such as surgery. The T-shaped band has a thin cord extending both sides, which is to be tied when being worn, and loosened by a nurse or a doctor just before surgery.

However, since the T-shaped band as described above looks like a loincloth or a diaper rather than underwear in appearance, it gives unpleasant feeling or uneasiness to the patient. There has been another problem that it took a lot of trouble for nurses or doctors with loosening a knot before surgery.

OBJECTS OF THE INVENTION

Accordingly, an object of the present invention is to provide disposable underwear that can reduce unpleasant feeling or uneasiness of the patient before surgery by making the appearance thereof look like everyday-use underwear, and that can easily be taken off by nurses or doctors.

Additional objects, advantages and novel features of the present invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In order to achieve the object described above, a disposable underwear according to the invention is formed by laying a front body and a back body one on top of the other, providing a bonded portion on at least one of the left and right side edges, and providing leg openings and a waist opening. It also comprises a tightening member in the vicinity of the waist opening. The front and back bodies further comprise a non-bonded portion formed at the portion between the tightening member and the bonded portion.

In the invention constructed as described above, since the overall shape is similar to that of everyday-use underwear, it advantageously reduce unpleasant feeling or uneasiness of the patient before surgery. In addition, when the nurse or the doctor takes his/her underwear off immediately before surgery, he/she can insert his/her finger into the non-bonded portion and tear it easily, whereby it can save his/her work to take the patient's underwear off.

DETAILED DISCLOSURE OF THE INVENTION

In the following detailed description of the preferred embodiments, reference is made to the accompanying drawings which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present inventions. The following detailed description is, therefore, not to be taken in a limiting sense, and scope of the present inventions is defined only by the appended claims.

Figure 1:
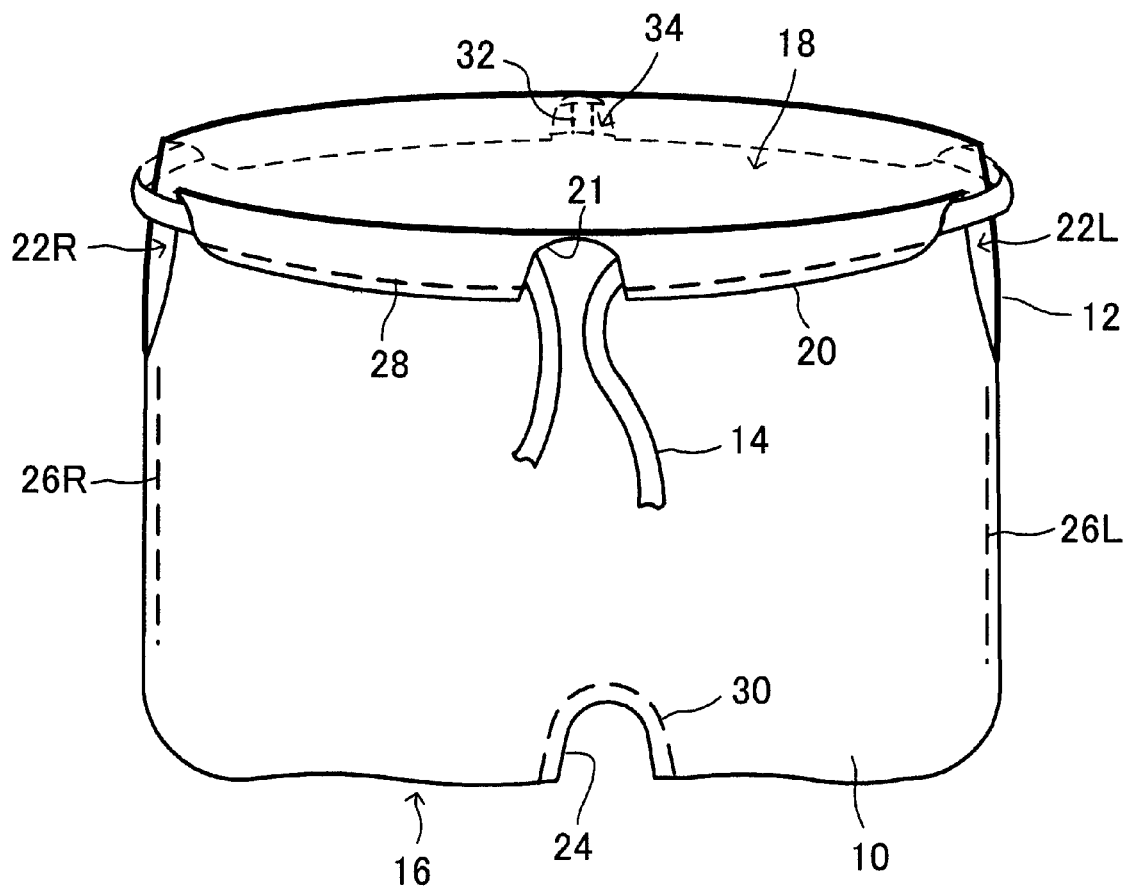
FIG. 1 is a perspective view showing the construction of disposable underpants according to a first embodiment of the present invention, when viewed from the front.
Figure 2:
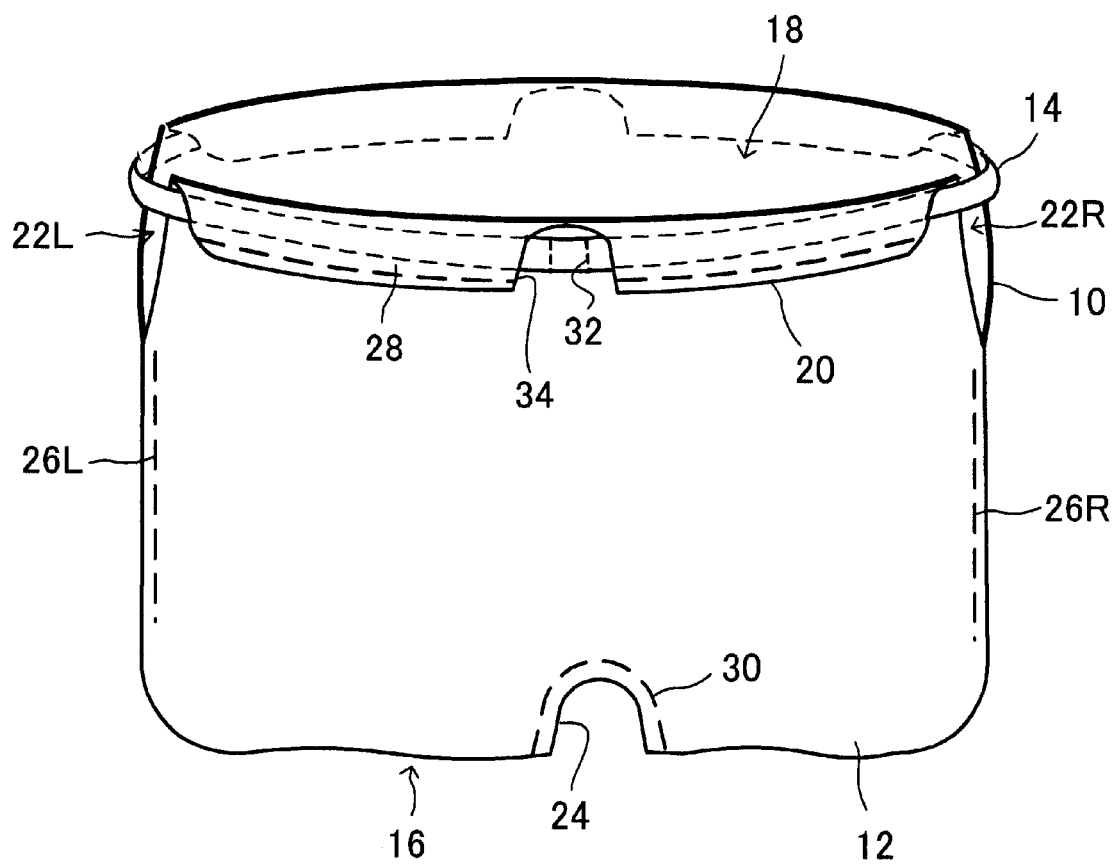
FIG. 2 is a perspective view showing the construction of disposable underpants according to the first embodiment of the present invention, when viewed from the back.
Figure 3:
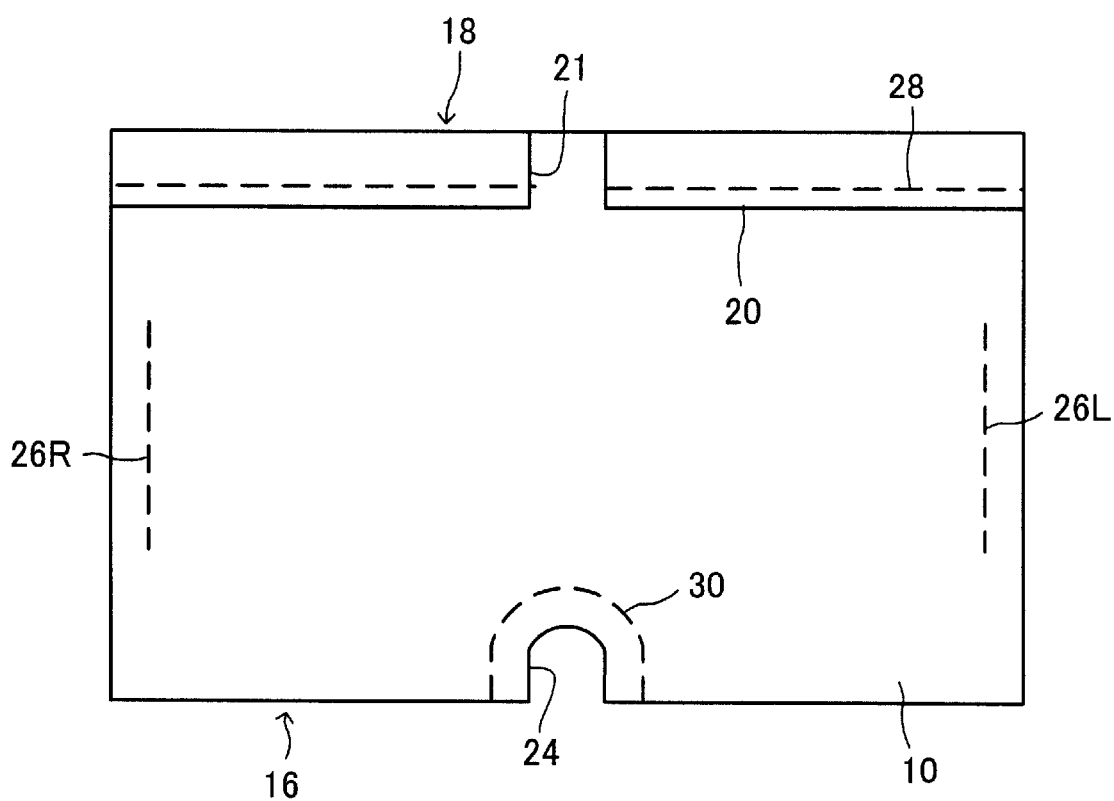
FIG. 3 is a plan view (front view) of the disposable underpants shown in FIG. 1 and FIG. 2 showing the positions of bonded lines.
Figure 4A:
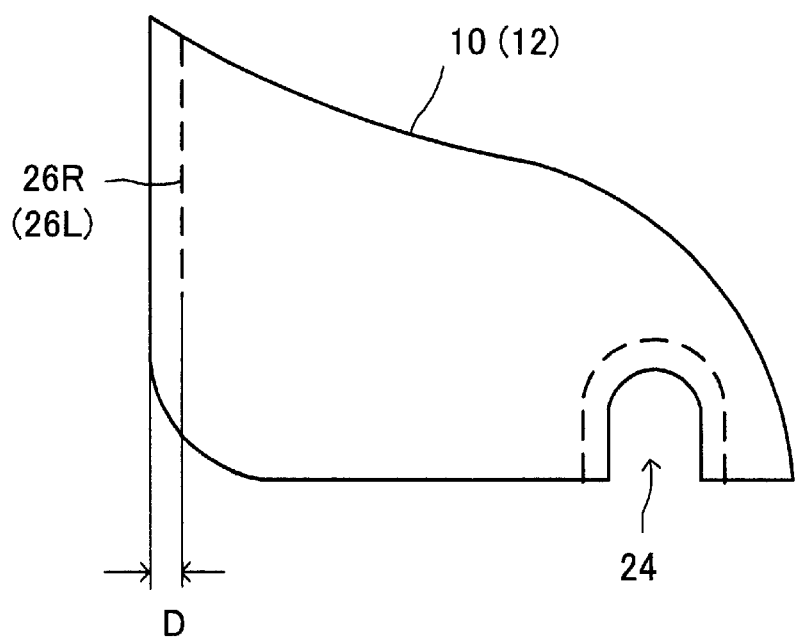
FIGS. 4A and 4B are explanatory drawings showing the construction of the principal portion of the disposable underpants according to the first embodiment.
Figure 4B:
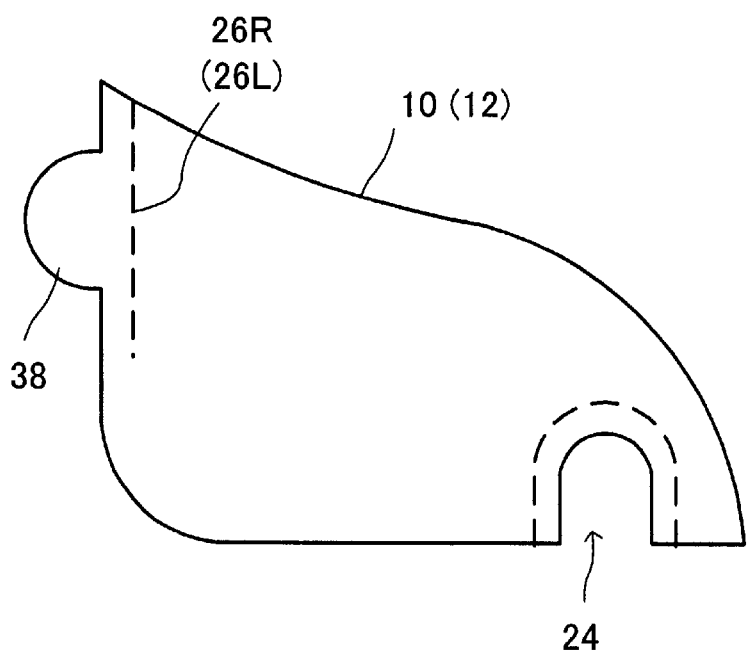

FIG. 1 and FIG. 2 are perspective views showing the construction of disposable underpants according to a first embodiment of the present invention, when viewed from the front and from the back respectively. FIG. 3 is a plan view (front view) of the disposable underpants in FIG. 1 and FIG. 2 showing the positions of bonded lines. FIGS. 4A and 4B are explanatory drawings showing the construction of principal portions of the same disposable underpants.

The disposable underpants of the first embodiment includes a front body 10 and a back body 12 formed of nonwoven fabric, and a tightening cord 14 to be disposed around the waist. The front body 10 and the back body 12 being formed of nonwoven fabric of the same configuration are laid one on top of the other, and then are bonded with each other at the side bonded portions 26R, 26L and the bonded portion between leg openings 30. It is also possible to employ a continuous sheet (nonwoven fabric) for the front body and the back body, fold it at the center thereof and then bond the edges. In this case, the side bonded portion is formed only on one side.

The bonded portion 30 is formed in the shape of inverted U, and the inner side thereof is formed with a notch 24. The side bonded portions 26R and 26L are formed only at the portions near the centers of the side edges of the front and back bodies. In other words, there are formed non-bonded portions 22R and 22L that are not to be bonded with each other between the upper ends of the bonded portions 26R and 26L and the upper edges of the front and back bodies 10 and 12. The non-bonded portions 22R and 22L are constructed so that one can insert his/her finger or fingers to rupture (separate) the bonded portions 26R and 26L before surgery.

The upper ends of the front and back bodies 10 and 12 are formed with sheaths (folded portion) 20 by folding them toward outsides thereof. The sheaths 20 are used for passing a cord 14 therethrough. At the position near the center of the sheath 20 of the front body 10, there is provided an opening 21 for guiding the left and right ends of the cord 14 out of the sheath. At the position near the center of the sheath 20 of the back body 12, there is provided an opening 34 for joining the cord 14 to the back body 12, and the cord 14 passing across the opening 34 is bonded to the back body 12 to form a bonded portion 32. The construction in which the back body 12 does not have a sheath 20, and the cords 14 extend from the upper side edges of the back body 12 and are passed through the sheath 20 of the front body 10 (not shown).

The bonded portions 26R, 26L and 30 may be formed by bonding the front body 10 and the back body 12 one on top of the other, or by butt-seaming. When forming the these bonded portions 26R, 26L and 30, for example, fusion welding such as a thermal sealing process or a sonic sealing process using ultrasonic wave may be employed. They may be bonded by adhesive agent such as hot melt adhesives. The bonding pattern at the bonded portions 26R, 26L and 30 may be either continuous or discontinuous.

When forming the bonded portions 26R, 26L and 30 by fusion welding, the width of the welded line is preferably between 0.1 mm and 15 mm, and more preferably, between 0.5 mm and 10 mm. When the width of the welded line is less than 0.1 mm, a line pressure exerted in the direction orthogonal to the direction of the flow of the sheet increases, which may results in rupture of the fusion-welded portion. On the other hand, when the width of the welded line is more than 15 mm, the wearers may have uncomfortable feeling. It is because the welded portion is higher in rigidity in comparison with the non-welded portion. The pattern of the welded portion that may be employed includes linear, wavelike, zigzag, or grillwork. It is also possible to use dotted pattern in combination to adjust the line pressure in the direction orthogonal to the direction of the flow of the sheet.

When forming the bonded portions 26R, 26L and 30 by the use of adhesive agent, bonding by means of hot melt adhesives is preferable. As a measure to apply hot melt materials that may be employed includes solid pattern or stripe pattern by coater dyeing, a netted pattern or dotted pattern by gravure coating, linear pattern by bead application, and spiral pattern, wavelike pattern, or zigzag pattern adjusted by air.

In the case of bonding by the use of adhesive agent, the width of the adhered portion is preferably between 1 mm and 15 mm. When the width of the adhered portion is less than 1 mm, the strength for bonding the sheets (10, 12) deteriorates, which may result in separation during use.

The strength at the bonded portions 26R, 26L and 30 is preferably between 0.5 N and 30 N when expressed in peel strength in the vertical direction of the underwear. When the peeling strength is less than 0.5 N, separation may occur during use, and when it is more than 30 N, it may resist separation when necessary. In the invention, the peeling strength is determined to be such that it resists easy separation during normal use before surgery, but is easily separable when a nurse tries to take it off immediately before surgery.

As shown in FIG. 4A, the positions of the bonded portions 26R and 26L are such that the distance D from both of the side edges in the laterally inward direction is approximately between 0.5 mm and 30 mm, and more preferably, between 1 mm and 20 mm. When the distance D is less than 0.5 mm, it may resist separation of the front and back bodies or may give uncomfortable feeling to the wearer because both side edges of these bodies come into contact with the patient's skin. In contrast to it, when the distance D is more than 30 mm, it may impair appearance of underwear. As shown in FIG. 4B, a pull 38 may be provided separately for making separation of bonded portions 26R and 26L easier.

As a tightening means for the waist, a mechanical fastener or the like may be employed instead of the cord 14.

The sheet that may be used for the front and back bodies 10 and 12 includes nonwoven fabric such as spunbonded fabric, spun-lace fabric, needle-punched fabric, melt-blown fabric, thermal-bonded fabric, chemical-bonded fabric formed of thermoplastic fibers. As fibers for such nonwoven fabric, polyolefin-based fiber, polyester-based fiber, polyamide-based fiber, and compound fiber such as thick-and-thin type, or side-by-side type formed of polyethylene/polypropylene or polyester may be used.

It is also possible to blend absorbent fibers to give nonwoven fabric sweat absorbent capability. The absorbent fibers includes pulp, rayon, cotton and acetate. In order for fusion welding the bonded portions, it is preferable to construct the sheet with 10 to 70 percent of absorbent fiber and 30 to 90 percent of thermoplastic fiber. When the absorbent fiber contained is less than 10 percent, sweat absorbent capability is lowered, and when it is more than 70 percent, the sealing performance is lowered.

Nonwoven fabric is preferably colored, for example, to blue or green of low saturation in order to avoid lack of hiding the patient's skin or private parts when the underwear is worn. The METSUKE, which is representing a weight for a unit of area, of nonwoven fabric is preferably in the range between 40 $g/m^2$ and 100 $g/m^2$. When METSUKE is less than 40 $g/m^2$, the nonwoven fabric may be transparent even when it is colored. In contrast to it, when the METSUKE is more than 100 $g/m^2$, the textile may be deteriorated, and it gives uncomfortable feeling to the wearer. Accordingly, the total beam transmission efficiency is determined to be not more than 60 percent, and more preferably, not more than 40 percent.

When wearing the disposable underwear according to this embodiment, the wearer inserts his/her legs from the waist opening 18 through the leg openings 16. Then, the ends of the cord 14 extending toward the front body side 19 are tied to tighten the portion around the waist. After the patient is laid on the surgical table, for example, the nurse puts her hand into the non-bonded portions 22R and 22L and separates the bonded portions 26R and 26L. Subsequently, she separates the bonded portion 30 to release bonding of the front body 10 and the back body 12, and then grips and pulls the cord 14 out from the non-bonded portions 22R and 22L. Consequently, the front body 10 is completely removed from the patient on the surgical table. The action to remove the cord 14 and the action to separate the bonded portions 26R and 26L may be carried out in the reverse order.

Figure 5:
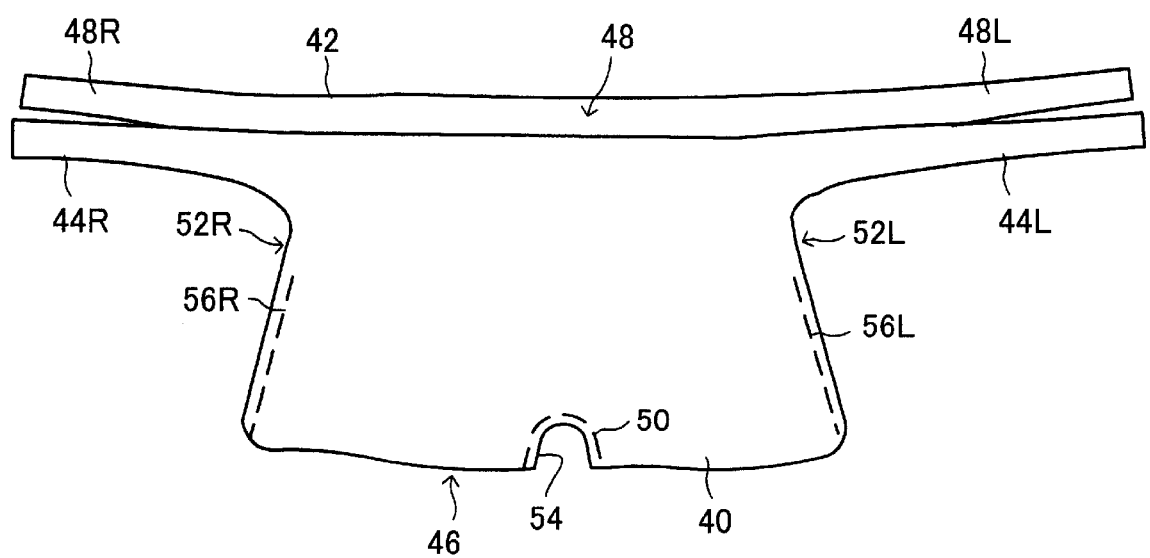
FIG. 5 is an exploded front view showing the construction of disposable underpants according to a second embodiment of the present invention.

FIG. 5 is an exploded front view showing the construction of disposable underpants according to a second embodiment of the present invention. Disposable underpants of this embodiment are formed by laying a front body 40 and a back body 42 in the same configuration one on top of the other. Materials of the front and back bodies 40 and 42 (nonwoven fabric) to be employed may be the same as those described in conjunction with the first embodiment, and thus will not be described again. Lace portions (belt portions) 44R and 44L for tightening the portion around the waist extend from the upper end of the left and right side edges of the front body 40. In the same manner, lace portions 48R and 48L for tightening the portion around the waist extend from the upper end of the left and right side edges of the back body 42.

The front body 40 and the back body 42 are laid one on top of the other, and then are bonded with each other at the side bonded portions 56R and 56L and at the bonded portion 50 between leg openings. It is also possible to employ a continuous sheet (nonwoven fabric) for the front body and the back body, fold it at the center thereof and then bond the edges. In this case, the side bonded portion is formed only on one side.

The bonded portion 50 is formed in the shape of inverted U, and the inner side thereof is formed with a notch 54. Side bonded portions 56R and 56L are formed only at a part of (at the lower part of) the side edges of the front and back bodies 40 and 42. In other words, there are formed non-bonded portions 52R and 52L between the upper ends of the bonded portions 56R and 56L and the lace portions 44R and 44L (48R and 48L). The non-bonded portions 52R and 52L are constructed so that one can insert his/her finger or fingers to separate (break) the bonded portions 56R and 56L immediately before surgery.

When wearing the disposable underwear according to this embodiment, the wearer inserts his/her legs into the waist opening 48 through the leg openings 46. Then, the lace portion 44R extending from the right edge of the front body 40 and the lace portion 48R extending from the right edge of the back body 42 are tied. In the same manner, the lace portion 44L extending from the left edge of the front body 40 and the lace portion 48L extending from the left edge of the back body 42 are tied. After the patient is laid on the surgical table, for example, the nurse puts her hand into the non-bonded portions 52R and 52L and separates the bonded portions 56R and 56L. Subsequently, she separates the bonded portion 50 to release bonding of the front body 40 and the back body 42, and then loosens a knot of the lace portions 44R and 48R and a knot of the lace portions 44L and 48L. Consequently, the front body 40 is completely removed from the patient on the surgical table. The action to loosen the knot of the lace portions and the action to separate the bonded portions 56R and 56L may be carried out in the reverse order.

Though the embodiments of the invention has been described thus far, the invention is not limited thereto, and may be modified in design as needed within the scope of the invention stated in the appended claims.

As is described thus far, according to the invention, unpleasant feeling or uneasiness of the passenger before surgery may be reduced because of its configuration similar to the everyday-use underwear. In addition, since the nurse or the doctor can easily break it by inserting her/his finger or fingers into the non-bonded portion when he/she takes the patient's underwear off immediately before surgery, it can advantageously save his/her work to take the patient's underwear off.

What is claimed is:

1. A disposable underwear, comprising:
   a body having front and back bodies one of which is laid on top of the other;
   a bonded portion and a non-bonded portion both of which are provided on at least one of left and right side edges of the body, the front and back bodies being bonded to each other at the bonded portion but not bonded at the non-bonded portion;
   leg openings formed between the front body and rear bode for passing a wearer's legs therethrough;
   a waist opening formed between the front and back body; and
   a tightening member which is provided adjacent the waist opening to be used for tightening the waist of the wearer,
   the non-bonded portion being formed between the tightening member and the bonded portion,
   the bonded portion having a peel strength in a range of between 0.5 N and 30 N.

2. A disposable underwear according to claim 1, wherein the bonded portion is formed on each of the left and right side edges of the front and back bodies.

3. A disposable underwear according to claim 1, wherein the front and back bodies are bonded adjacent the center of the leg openings.

4. A disposable underwear according to claim 1, wherein the tightening member is formed integrally with the front and back bodies,
   the tightening member comprises lace members extending substantially horizontally from a side of the upper edge of the front and back bodies, and
   the waist opening is tightened by tying the lace members opposing to each other.

5. A disposable underwear according to claim 4, wherein the lace members are provided at right and left sides of each of the front and back bodies, and
   a pair of the lace members extending from the same side are tying with each other.

6. A disposable underwear according to claim 1, wherein the tightening member comprises a sheath, which is formed by folding downwardly and bonding an upper edge of a waist portion of the front and back bodies; and a cord passing through the sheath.

7. A disposable underwear according to claim 1, wherein each of the front and back bodies is formed of nonwoven fabric of 40 g/m² to 100 g/m² in METSUKE.

8. A disposable underwear according to claim 1, wherein each of the front and back bodies is formed of nonwoven fabric having the total beam transmission efficiency of less than 60 percent.

9. A disposable underwear according to claim 1, wherein the bonded portion is formed at a position 5 mm to 30 mm inward from the side edges of the front and back bodies.

10. A disposable underwear, comprising:
    a body having front and back bodies one of which is laid on top of the other;
    first bonded and non-bonded portions provided on at least one of left and right side edges of the body, the front and back bodies being bonded to each other at the first bonded portion but not bonded at the non-bonded portion;
    leg openings formed between the front body and rear bode for passing a wearer's legs therethrough;
    a second bonded portion provided between the leg openings, the second bonded portion having a peel strength that is between 0.5 N and 30 N;
    a waist opening formed between the front and back body; and
    a tightening member which is provided adjacent the waist opening to be used for tightening the waist of the wearer,
    the non-bonded portion being formed between the tightening member and the first bonded portion.

* * * * *